(12) United States Patent
Strommer et al.

(10) Patent No.: US 7,840,252 B2
(45) Date of Patent: *Nov. 23, 2010

(54) METHOD AND SYSTEM FOR DETERMINING A THREE DIMENSIONAL REPRESENTATION OF A TUBULAR ORGAN

(75) Inventors: Gera Strommer, Haifa (IL); Uzi Eichler, Haifa (IL); Itzik Shmarak, Nofit (IL); David Peles, Haifa (IL)

(73) Assignee: MediGuide, Ltd., Haifa (IL)

( * ) Notice: Subject to any disclaimer, the term of this patent is extended or adjusted under 35 U.S.C. 154(b) by 1380 days.

This patent is subject to a terminal disclaimer.

(21) Appl. No.: 11/233,948

(22) Filed: Sep. 23, 2005

(65) Prior Publication Data

US 2006/0064006 A1    Mar. 23, 2006

Related U.S. Application Data (63) Continuation-in-part of application No. 11/233,420, filed on Sep. 16, 2005, which is a continuation-in-part of application No. 10/986,567, filed on Nov. 10, 2004, which is a continuation-in-part of application No. 10/938,395, filed on Sep. 9, 2004, now Pat. No. 7,778, 688, which is a continuation-in-part of application No. 09/949,160, filed on Sep. 7, 2001, now Pat. No. 7,343, 195, which is a continuation-in-part of application No. 09/782,528, filed on Feb. 13, 2001, which is a continuation-in-part of application No. 09/314,474, filed on May 18, 1999, now Pat. No. 6,233,476.

(51) Int. Cl.
*A61B 5/05* (2006.01)

(52) U.S. Cl. .................. 600/424; 600/407; 600/415; 600/429; 600/434; 600/439

(58) Field of Classification Search ................ 600/415, 600/424, 429, 439
See application file for complete search history.

(56) References Cited

U.S. PATENT DOCUMENTS 3,937,066 A    2/1976    Green et al.

(Continued)

FOREIGN PATENT DOCUMENTS

EP    1088515 A1    4/2001

(Continued)

OTHER PUBLICATIONS

Panza, Julio A., "Real-time three-dimensional echocardiography: An overview", *The International Journal of Cardiovascular Imaging* 17:227-235, 2001.

*Primary Examiner*—Brian Casler
*Assistant Examiner*—John F Ramirez
(74) *Attorney, Agent, or Firm*—Dykema Gosset PLLC (57) ABSTRACT

A method for determining a three dimensional representation of a tubular organ, the method comprising the procedures of registering a three dimensional medical positioning system (MPS) coordinate system with a two dimensional coordinate system, acquiring a plurality of MPS points within the tubular organ, the MPS points are associated with the MPS coordinated system, each of the MPS point is acquired with a respective organ timing signal reading, acquiring at least one two dimensional image of the tubular organ, the at least one two dimensional image is associated with the two dimensional coordinate system, the at least one two dimensional image is acquired from at least one perspective, each of the at least one two dimensional image is further acquired with a respective organ timing signal reading, associated each of the MPS points with the at least one two dimensional image according to the organ timing signals thereof, determining a temporal three dimensional representation of a portion of the tubular organ for each MPS point, the portion being identifiable in the respective two dimensional image.

32 Claims, 10 Drawing Sheets

U.S. PATENT DOCUMENTS

| | | | |
|---|---|---|---|
| 3,974,826 A | 8/1976 | Eggleton et al. | |
| 3,990,296 A | 11/1976 | Erikson | |
| 4,398,540 A | 8/1983 | Takemura et al. | |
| 4,737,794 A | 4/1988 | Jones | |
| 5,016,642 A | 5/1991 | Dukes et al. | |
| 5,152,290 A | 10/1992 | Freeland | |
| 5,159,931 A | 11/1992 | Pini | |
| 5,318,025 A | 6/1994 | Dumoulin et al. | |
| 5,398,691 A | 3/1995 | Martin et al. | |
| 5,453,686 A | 9/1995 | Anderson | |
| 5,529,070 A | 6/1996 | Augustine et al. | |
| 5,577,502 A | 11/1996 | Darrow et al. | |
| 5,588,432 A | 12/1996 | Crowley | |
| 5,622,174 A | 4/1997 | Yamazaki | |
| 5,646,525 A | 7/1997 | Gilboa et al. | |
| 5,669,385 A * | 9/1997 | Pesque et al. | 600/453 |
| 5,690,113 A | 11/1997 | Sliwa, Jr. et al. | |
| 5,730,129 A | 3/1998 | Darrow et al. | |
| 5,740,808 A | 4/1998 | Panescu et al. | |
| 5,744,953 A | 4/1998 | Hansen | |
| 5,787,889 A | 8/1998 | Edwards et al. | |
| 5,806,521 A | 9/1998 | Morimoto et al. | |
| 5,830,145 A | 11/1998 | Tenhoff | |
| 5,830,222 A | 11/1998 | Makower | |
| 5,846,200 A | 12/1998 | Schwartz | |
| 5,899,860 A | 5/1999 | Pfeiffer et al. | |
| 5,906,578 A | 5/1999 | Rajan et al. | |
| 5,913,820 A | 6/1999 | Bladen et al. | |
| 5,924,989 A | 7/1999 | Polz | |
| 5,928,248 A | 7/1999 | Acker | |
| 5,935,075 A | 8/1999 | Casscells | |
| 5,938,606 A * | 8/1999 | Bonnefous | 600/437 |
| 5,949,491 A | 9/1999 | Callahan et al. | |
| 5,955,879 A | 9/1999 | Durdle et al. | |
| 5,957,844 A | 9/1999 | Dekel et al. | |
| 5,967,980 A | 10/1999 | Ferre et al. | |
| 5,976,088 A | 11/1999 | Urbano et al. | |
| 5,993,390 A | 11/1999 | Savord et al. | |
| 5,994,690 A | 11/1999 | Kulharni et al. | |
| 6,030,343 A | 2/2000 | Chechersky et al. | |
| 6,035,856 A | 3/2000 | LaFontaine et al. | |
| 6,047,080 A | 4/2000 | Chen et al. | |
| 6,134,003 A | 10/2000 | Tearney et al. | |
| 6,148,095 A | 11/2000 | Prause et al. | |
| 6,169,917 B1 | 1/2001 | Masotti et al. | |
| 6,175,669 B1 | 1/2001 | Colston et al. | |
| 6,185,271 B1 | 2/2001 | Kinsinger | |
| 6,216,029 B1 | 4/2001 | Paltieli | |
| 6,228,028 B1 | 5/2001 | Klein et al. | |
| 6,246,898 B1 * | 6/2001 | Vesely et al. | 600/424 |
| 6,275,724 B1 | 8/2001 | Dickinson et al. | |
| 6,317,621 B1 | 11/2001 | Graumann et al. | |
| 6,321,109 B2 | 11/2001 | Ben-Haim et al. | |
| 6,385,476 B1 | 5/2002 | Osadchy et al. | |
| 6,390,982 B1 | 5/2002 | Bova et al. | |
| 6,405,072 B1 | 6/2002 | Cosman | |
| 6,416,476 B1 | 7/2002 | Ogasawara et al. | |
| 6,432,041 B1 | 8/2002 | Taniguchi et al. | |
| 6,470,207 B1 | 10/2002 | Simon et al. | |
| 6,501,981 B1 | 12/2002 | Schweikard et al. | |
| 6,546,271 B1 | 4/2003 | Reisfeld | |
| 6,556,695 B1 | 4/2003 | Packer et al. | |
| 6,589,163 B2 | 7/2003 | Aizawa et al. | |
| 6,626,902 B1 | 9/2003 | Kucharczyk et al. | |
| 6,733,458 B1 | 5/2004 | Steins et al. | |
| 6,773,393 B1 | 8/2004 | Taniguchi et al. | |
| 6,775,404 B1 | 8/2004 | Pagoulatos et al. | |
| 6,895,267 B2 | 5/2005 | Panescu et al. | |
| 7,007,699 B2 | 3/2006 | Martinelli et al. | |
| 7,195,587 B2 | 3/2007 | Taniguchi et al. | |
| 7,235,084 B2 | 6/2007 | Skakoon et al. | |
| 7,386,339 B2 | 6/2008 | Strommer et al. | |
| 7,398,116 B2 | 7/2008 | Edwards | |
| 2001/0044578 A1 | 11/2001 | Ben-Haim et al. | |
| 2002/0007124 A1 | 1/2002 | Woodward | |
| 2002/0049375 A1 | 4/2002 | Strommer et al. | |
| 2002/0193686 A1 | 12/2002 | Gilboa | |
| 2004/0097804 A1 | 5/2004 | Sobe | |
| 2004/0116775 A1 | 6/2004 | Taniguchi et al. | |
| 2004/0138548 A1 | 7/2004 | Strommer et al. | |
| 2005/0033149 A1 | 2/2005 | Strommer et al. | |
| 2005/0049493 A1 | 3/2005 | Kerby et al. | |
| 2005/0107688 A1 | 5/2005 | Strommer | |
| 2005/0197557 A1 | 9/2005 | Strommer et al. | |
| 2006/0058647 A1 | 3/2006 | Strommer et al. | |
| 2006/0064006 A1 | 3/2006 | Strommer et al. | |
| 2008/0175463 A1 | 7/2008 | Strommer et al. | |

FOREIGN PATENT DOCUMENTS

| | | | |
|---|---|---|---|
| WO | 97/29682 A1 | 8/1997 | |
| WO | 99/43253 A1 | 9/1999 | |
| WO | 00/10456 A1 | 3/2000 | |
| WO | 00/16684 A1 | 3/2000 | |
| WO | 02/064011 A2 | 8/2002 | |
| WO | WO-2004/060157 | 7/2004 | |
| WO | WO-2005/039391 | 5/2005 | |

* cited by examiner

METHOD AND SYSTEM FOR DETERMINING A THREE DIMENSIONAL REPRESENTATION OF A TUBULAR ORGAN

CROSS REFERENCE TO RELATED APPLICATIONS

This application is a continuation-in-part of U.S. Patent Application filed on Sep. 13, 2005, entitled "METHOD AND SYSTEM FOR DETERMINING A THREE-DIMENSIONAL REPRESENTATION OF A TUBULAR ORGAN", which is a continuation-in-part of U.S. patent application Ser. No. 10/986,567, filed on Nov. 10, 2004, which is a continuation-in-part of U.S. patent application Ser. No. 10/938,395, filed on Sep. 9, 2004. All of the prior applications identified above are incorporated herein by reference in their entireties.

FIELD OF THE DISCLOSED TECHNIQUE

The disclosed technique relates to organ assessment, in general, and to methods and systems for determining a 3D representation of a tubular organ, in particular.

BACKGROUND OF THE DISCLOSED TECHNIQUE 3D visual representation of an organ assists a physician in assessing the condition of that organ. More particularly, a 3D representation of a tubular organ, such as a coronary vessel, helps identify and assess plaque burden and lesion dimensions such as length, diameter and volume. Further more, a 3D representation of a tubular organ aids the physician to identify, on a 2D image, regions of foreshortening of the vessel caused by the projection of the 3D vessel on a 2D plane. Additionally, with the aid of the 3D representation of the tubular organ, a physician can identify bifurcation points of that tubular organ.

U.S. Pat. No. 6,169,917, entitled "Method and Device for Reconstructing Three-Dimensional Images of Blood Vessels, Particularly coronary vessel, or Other Three-Dimensional Structure" to Masotti et al, directs to a method wherein three X-Ray images, from three different perspective are provided. A reference object, comprising two planes, integral with the patient, containing at least six points with known three-dimensional coordinates, opaque to the image radiation, provides the perspective transformations associated with each angiographic image. Using these transformations, and a set of points of projection of a three-dimensional object, the three-dimensional object is reconstructed.

The reconstruction is determined using a semi-automatic algorithm. Initially, a starting point and an initial direction of the vessel are determined. From thereon, the next segment of the vessel, whose length is proportional to the actual radius thereof, is identified. The segment is identified according to the probability that the vessel proceeds in a given direction. This probability is determined by calculating the mean gray level contained in a rectangular mask which is rotated about the point belonging to the center line of the vessel.

U.S. Pat. No. 6,148,095 entitled "Apparatus and Method for Determining Three-Dimensional Representation of Tortuous Vessel" to Prause et al, directs to an apparatus and method for reconstruction of the coronary vessel, generated from ECG-gated intravascular ultrasound (IVUS) frames obtained by a catheter, combined with biplane angiography. Initially, the IVUS catheter is positioned at the distal endpoint of the designated vessel. The IVUS catheter is withdrawn at a fixed speed while biplane X-ray images are acquired. The IVUS catheter obtains ultrasound images from within the vessel during the withdrawal. Since either the catheter, or the lumen borders or both are present on the biplane X-ray images, a 3D representation of the centerline of the vessel can be reconstructed. Using this 3D centerline representation in conjunction with information about the physical properties of the catheter a 3D pullback path of the catheter is determined. The IVUS images are then mapped to the determined 3D pullback path according to the pullback speed and catheter twist. The gaps between adjacent IVUS slice are filled by interpolation. The IVUS images are further correlated with the activity phase of the heart. The activity phase of the heart is obtained by Electrocardiogram (ECG), to ensure that the images are obtained under consistent conditions.

U.S. Pat. No. 6,047,080 entitled "Method and Apparatus for Three-Dimensional Reconstruction of Coronary Vessel from Angiographic Image" to Chen et al, directs to a method for reconstruction of a 3D coronary arterial tree from routine biplane angiograms acquired at arbitrary angles and without using calibration objects. According to the method directed to by Chen et al, a plurality of 2D images of a target object is acquired. On each image, the centerlines of the vessels are identified. Using these centerlines, a vessel hierarchy data structure, including the identified 2D vessel centerlines is created. By traversing the corresponding vessel hierarchy data structure, a predetermined number of bifurcation points are calculated. Using the calculated bifurcations points, corresponding to each of the projected image, the rotation matrix and translation vector representing the relative orientation of the images are determined. Using these rotation matrix and translation vector, the correspondence between the 2D centerlines, corresponding to each image, is established and a 3D vessel centerline is calculated. A 3D visual representation, of the target object, is reconstructed based on the 3D vessel centerline and diameter of each vessel, estimated along the 3D centerline of each vessel. Consequently, the optimal views, of the vessel segments, with minimal vessel foreshortening, are determined.

U.S. Pat. No. 6,456,271 entitled "Vascular Reconstruction" to Reidfeld, directs to a method and apparatus for reconstructing blood vessels in three dimensions. A catheter, including a position sensor, is advanced into the blood vessel and the position of the sensor is acquired at a plurality of points in the vessel. Based on these points, a centerline and the inner surface of the blood vessel are calculated. The plurality of points is fitted to a parametric representation of the vessel centerline. Each coordinate dimension, in the parametric representation, is represented by a polynomial. The inner surface of the blood vessel is reconstructed about the centerline by generating a tube of either fixed or variable radius. This tube is generated by determining plurality of unit vectors, sampling the circle around the centerline, and multiplying these unit vectors by the radius of the tube. The radius is determined by averaging the distances of the points from the centerline. A reconstruction, with variable radius, is achieved by averaging the distances of a plurality of points in a vicinity of interest. Alternatively, the radius may be selected by the user. Using the centerline and the radius a wire frame of the blood vessel is generated and the rectangular patches composing the wire frame are shaded.

SUMMARY OF THE PRESENT DISCLOSED TECHNIQUE

It is an object of the disclosed technique to provide a novel method and system for determining a three dimensional representation of a tubular organ.

In accordance with the disclosed technique, there is thus provided a method for determining a three dimensional representation of a tubular organ comprising the procedures of registering a three dimensional medical positioning system (MPS) coordinate system with a two dimensional coordinate system. Acquiring a plurality of MPS points within the tubular organ, the MPS points are associated with the MPS coordinated system, each of the MPS point is acquired with a respective organ timing signal reading. Acquiring at least one two dimensional image of the tubular organ, the at least one two dimensional image is associated with the two dimensional coordinate system, the at least one two dimensional image is acquired from at least one perspective angle, each of the at least one two dimensional image is further acquired with a respective organ timing signal reading. Associating each of the MPS points with the at least one two dimensional image according to the organ timing signals thereof. Determining a temporal three dimensional representation of a portion of the tubular organ for each MPS point.

In accordance with another aspect of the disclosed technique, there is thus provided a system for determining a three dimensional representation of a tubular organ. The system comprising an organ timing signal detector, a medical imaging system, a medical positioning system (MPS), a catheter fitted with an MPS sensor, and a processor. The medical imaging system is associated with a two dimensional coordinate system. The MPS is associated with a three dimensional MPS coordinate system. The processor is coupled with the MPS, with the organ timing signal detector and with the medical imaging system. The MPS is coupled with the organ timing signal detector and with the MPS sensor fitted on the catheter. The processor is coupled with the MPS, the organ timing signal detector and with the medical imaging system. The organ timing signal detector acquires an organ timing signal reading representing the activity state of the organ. Medical imaging system acquires at least one two dimensional image from at least one perspective. The at least one two dimensional image is associated with a respective organ timing signal reading. The catheter is inserted into the tubular organ and the MPS acquires a plurality of MPS points. Each of the MPS points is associated with a respective organ timing signal reading. The processor registers the three dimensional MPS coordinate system with the two dimensional coordinate system, associates an organ timing signal reading with each of the MPS points and with each of the at least one two dimensional image and determines a three dimensional representation of the tubular organ.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art, by providing a method and a system for determining a 3D representation of a tubular organ. A plurality of Medical Positioning System (MPS) points, representing the positions of an MPS sensor, within the tubular organ, are acquired. The MPS sensor is fitted on a catheter and is associated with a 3D MPS coordinate system. This catheter may be a Guided Measurement Catheter (GMC), a diagnostic catheter (e.g., Ultra Sound imaging catheter) or a therapeutic catheter (e.g., stenting catheter or an ablating catheter). Additionally, a contrast dye is injected into the tubular organ and at least one 2D image (e.g., X-ray image, magnetic resonance image, positron emission tomography image or ultrasound image), from at least one perspective angle, of that tubular organ, is acquired. The 2D image is associated with a 2D coordinate system. The contrast dye highlights the tubular organ in the image. The 2D coordinate system is registered with the 3D MPS coordinate system ( e.g., by an optical-magnetic calibration procedure). After the MPS points are acquired, a 3D representation of the tubular organ is determined and displayed.

The MPS points represent the 3D trajectory of the MPS sensor within the tubular organ. This 3D trajectory is projected on the 2D image, thereby defining the centerline of the tubular organ on that 2D image. The 2D borders of the tubular organ, identifiable on the 2D image, are detected according to the defined centerline, by an image segmentation process. A 3D circle is generated around each MPS point, the diameter of the 3D circle being the distance between the detected borders at the respective MPS point. This 3D circle defines the 3D border of the 3D representation of the tubular organ.

When only a single 2D image is used, the resulting 3D representation of the tubular organ is limited to a circular cross section. However, the tubular organ might have an oval cross section or other arbitrary cross sections. Therefore, a plurality of 2D images, from different perspective angles of the tubular organ, are acquired. The contour of the 3D border is refined according to the detected 2D border points of the tubular organ on each 2D image, and the resulting cross section is a closed curve.

During acquisition of the MPS points and the 2D image, or images, the inspected tubular organ may move. This motion affects the MPS sensor readings (e.g., position and orientation). Therefore, while acquiring MPS point readings and 2D images, the system simultaneously acquires organ timing signals of organs (e.g., the heart, the lungs). These organ timing signals represent the activity state of the organs. Accordingly, each of the MPS points and each 2D image are associated with a respective organ timing signal reading. Consequently, each MPS point is associated with a respective 2D image according to the organ timing signals thereof. Thus, a unique 3D trajectory, of the MPS sensor, is defined for each activity state and therefore for each 2D image. This unique 3D trajectory is projected on the respective 2D image when the centerline of the tubular organ is defined as described above.

Figure 1:
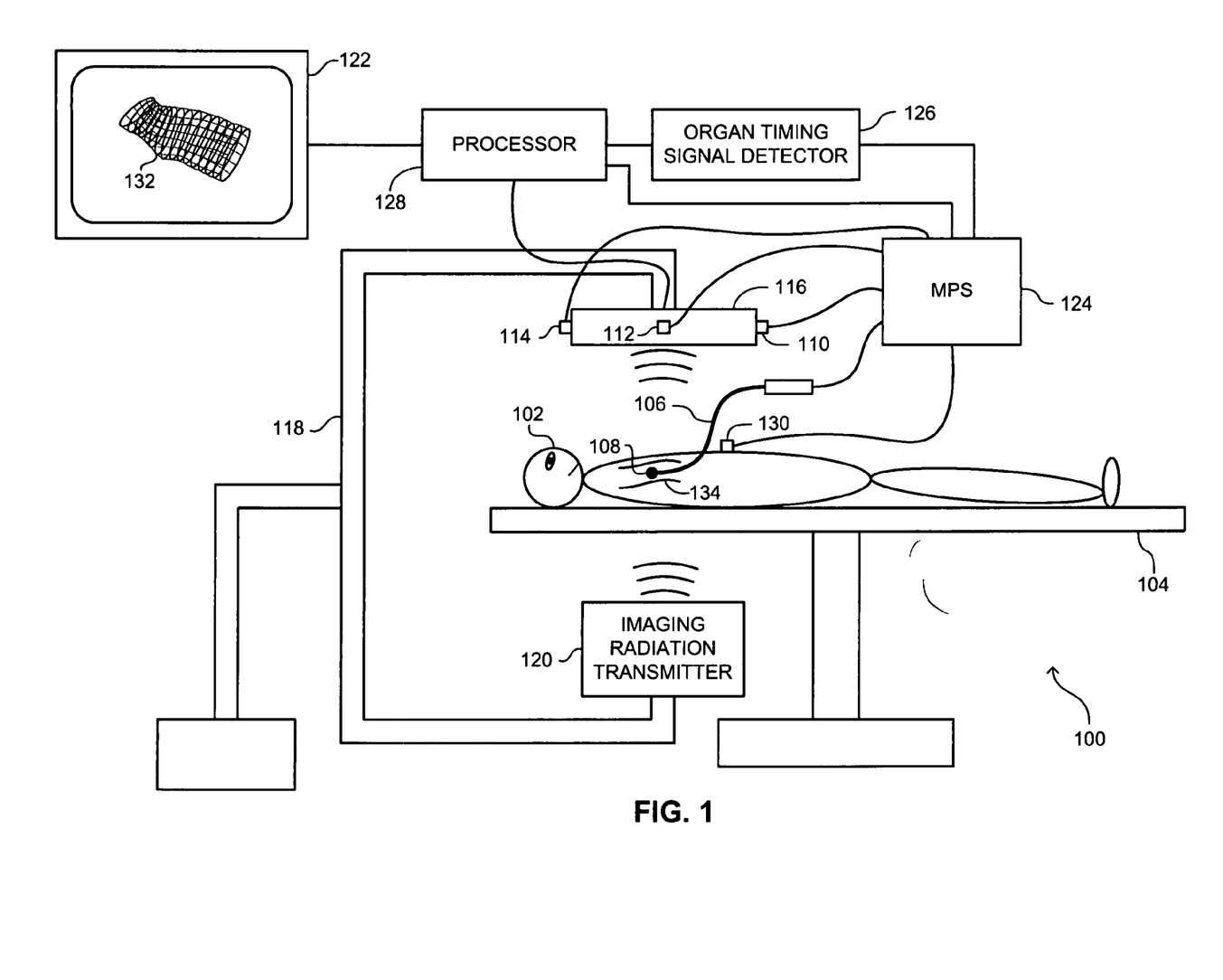
FIG. 1, is a schematic illustration of a system for determining a 3D representation of a tubular organ.

Reference is now made to FIG. 1, which is a schematic illustration of a system for determining a 3D representation of a tubular organ, generally referenced 100, constructed and operative in accordance with another embodiment of the disclosed technique. In the following description of system 100, the inspected tubular organ is assumed stationary (i.e., the tubular organ is not moving). System 100 includes medical imaging system 118 associated with a 2D coordinate system, a Medical Positioning System (MPS) 124 associated with a 3D MPS coordinate system, an organ timing signal detector 126, a processor 128, a catheter 106, a display unit 122 and a table 104. Medical imaging system 118 includes an imaging radiation transmitter 120 and an imaging radiation detector 116. Medical positioning system 124 includes MPS transmitters 110, 112 and 114, reference sensor 130 and an MPS sensor (not shown).

Processor 128 is coupled with organ timing signal detector 126, with imaging radiation detector 116, with MPS 124 and with Display unit 122. MPS 124 is coupled with organ timing signal detector 126 and with catheter 106. The MPS sensors (not shown) are coupled with distal end 108 of catheter 106. MPS transmitters 110, 112 and 114 are coupled with imaging radiation detector 116.

Catheter 106 is inserted into tubular organ 134 and MPS 124 acquires a plurality of MPS points within tubular organ 134. Medical imaging system 118 acquires at least one 2D image of tubular organ 134 from at least one perspective. The 2D images are provided to processor 128. Processor 128 registers the 3D MPS coordinate system with the 2D coordinate system and projects the 3D trajectory of the catheter on each of the 2D images. Thus, the centerline of the tubular organ on the respective 2D image is defined. Using this centerline and image processing techniques, processor 128 detects the 2D borders of a portion of organ 134 identifiable on the respective 2D image. Using these 2D borders and the MPS points, processor 128 determines a 3D representation of a portion of the tubular organ. Display 122 displays 3D representation 132 of organ 134. Display 122 may further display 3D representation 132 of organ 134 superimposed on a 2D image.

Figure 2A:
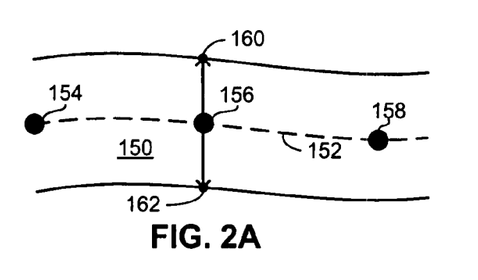
FIGS. 2A, 2B, 2C, 2D, 2E and 2F are schematic illustrations of exemplary two 2D images of tubular organ 150 acquired from two different perspective angles and the resulting cross section and 3D representation of tubular organ 150.
Figure 2B:
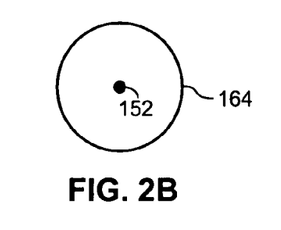
Figure 2C:
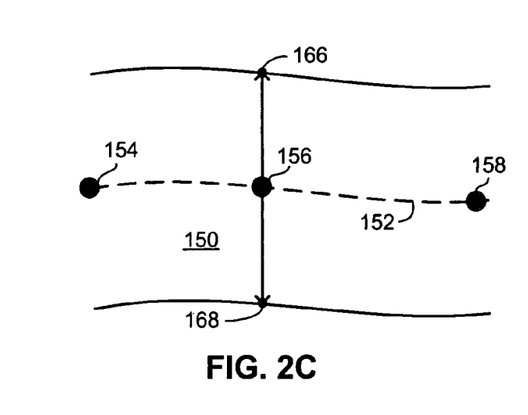
Figure 2D:
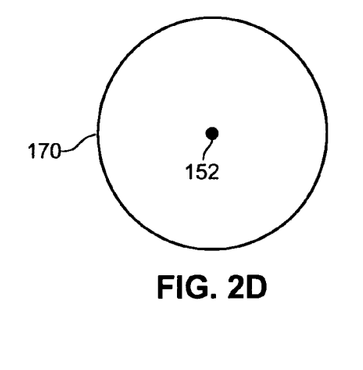
Figure 2E:
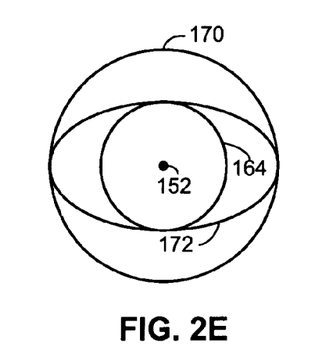
Figure 2F:
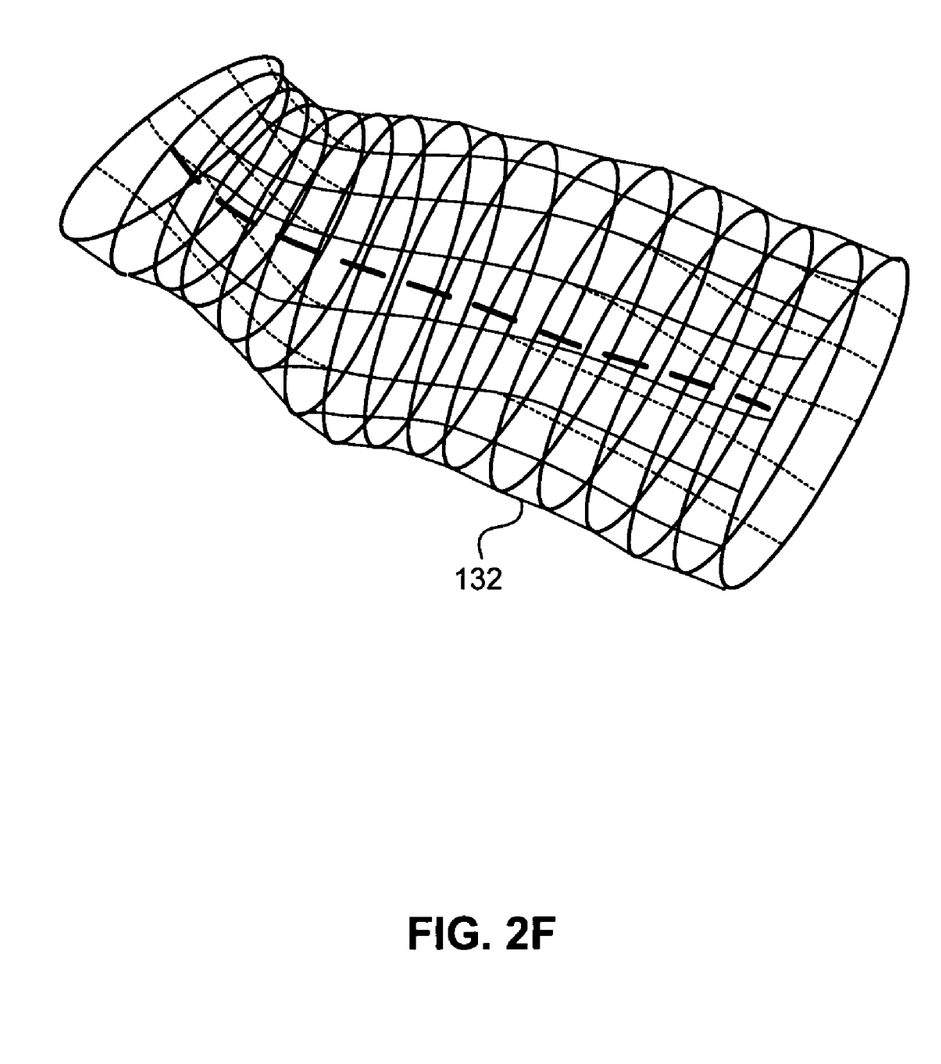

Reference is now made to FIGS. 2A, 2B, 2C, 2D, 2E and 2F which are schematic illustrations of exemplary two 2D images of tubular organ 150 acquired from two different perspective angles and the resulting cross section and 3D representation of tubular organ 150 in accordance with another embodiment of the disclosed technique. In the following description of FIGS. 2A, 2B, 2C, 2D, 2E and 2F, the inspected tubular organ is assumed stationary. Both 2D images (FIGS. 2A and 2C) include centerline 152 which is defined by projection of the 3D trajectory of a catheter. The 3D trajectory is determined by MPS points 154, 156 and 158. Using centerline 152, border points 160 and 162 (FIG. 2A) and border points 166 and 168 (FIG. 2C) of tubular organ 150 are detected. These detected border points are used to define the constraints of the closed curve that will define the 3D borders of tubular organ 150. In this exemplary case, these constraints are the distance between border points 160 and 162 (FIG. 2A), and the distance between border points 166 and 168 (FIG. 2C). These distances define diameters of circles. Using these defined diameters, a circle is generated around each MPS point. In FIG. 2B, the diameter of circle 164 corresponds to the distance between border points 160 and 162 (FIG. 2A) at MPS point 156 (FIG. 2A) as detected from the first perspective. In FIG. 2D, the diameter of circle 170 corresponds to the distance between the border points 166 and 168 (FIG. 2C) at MPS point 156 (FIG. 2C) as detected from the second perspective. Thus, a contour 172 (FIG. 2E) is traced from circle 160 and 162. Contour 172 has the shape of an ellipse since it is generated from two circles. After repeating for each MPS point, a 3D model, such as 3D model 132 (FIG. 2F and FIG. 1) is determined.

The inspected organ may move during the acquisition of the MPS points and the 2D image or images. More particularly, when the tubular organ is a coronary artery, the tubular organ is involved in a cyclic motion according to the cardiac cycle, caused by the pressurized flow of blood therein. Therefore, the MPS points are associated with the 2D images (e.g., by synchronization), according to the organ timing signals acquired simultaneously therewith.

Figure 3A:
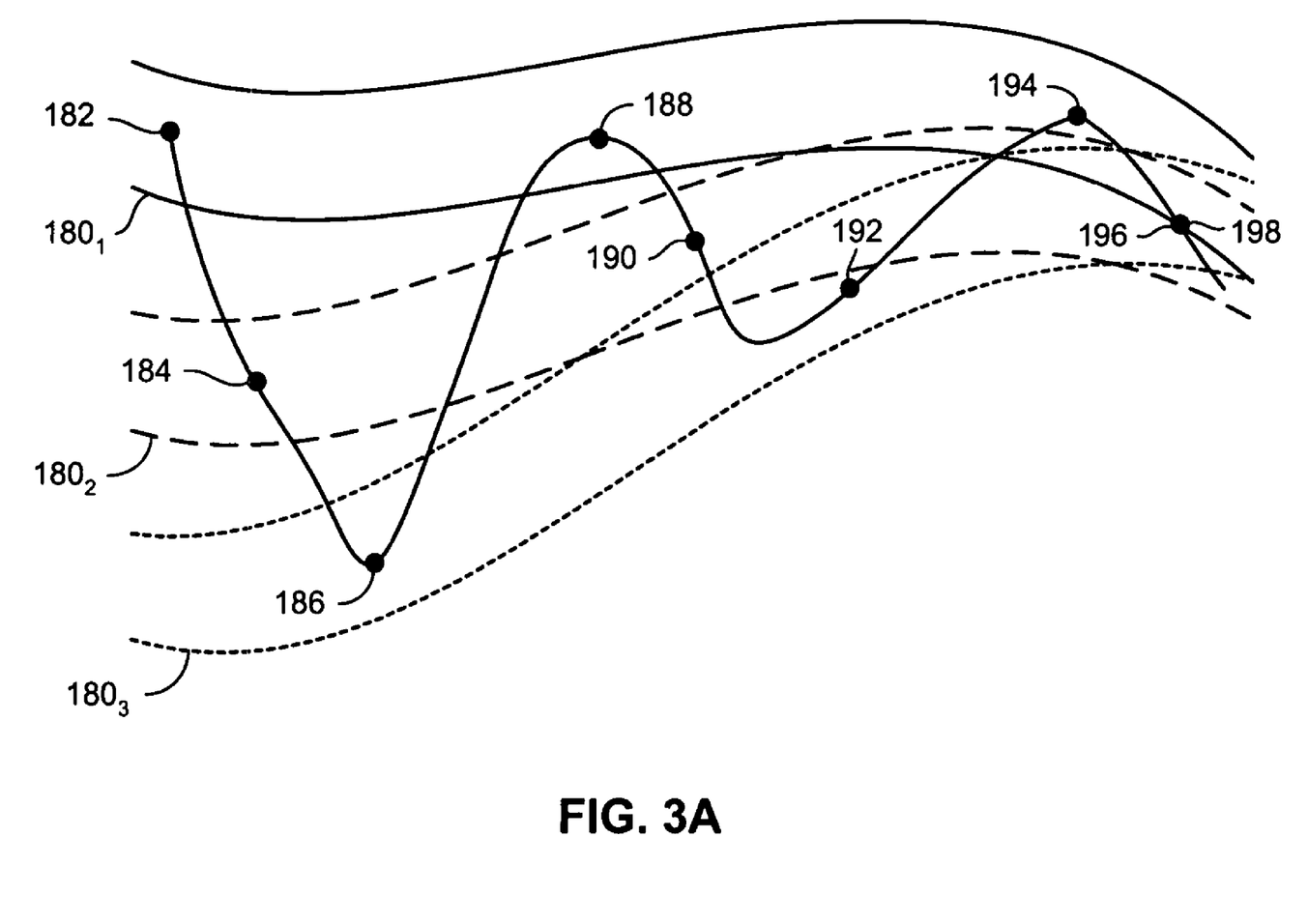
FIGS. 3A and 3B are a schematic illustration of three 2D images, of tubular organ in the body of a patient, acquired at three different activity states of the organ, and the MPS points acquired during these three different activity states.
Figure 3B:
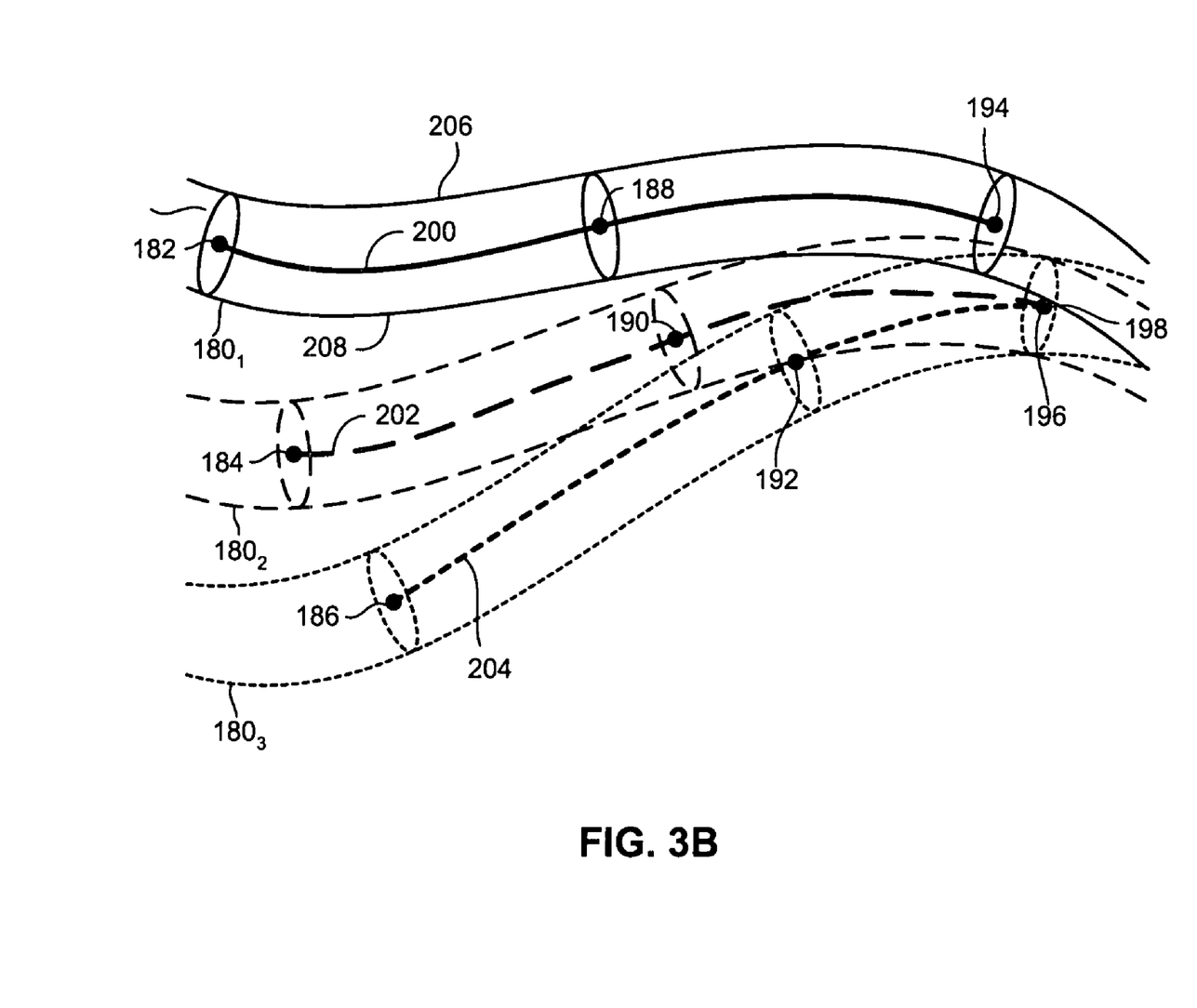

Reference is now made to FIGS. 3A and 3B, which are a schematic illustration of three 2D images, of tubular organ in the body of a patient, acquired at three different activity states of the organ, and the MPS points acquired during these three different activity states, in accordance with a further embodiment of the disclosed technique. The first image of the organ, designated $180_1$, was acquired at a first activity state $T_1$. The second image of the organ, designated $180_2$, was acquired at a second activity state $T_2$. The third image of the organ, designated $180_3$, was acquired at a third activity state $T_3$. During activity state $T_1$, MPS points 182, 188 and 194 were acquired. During activity state $T_2$, MPS points 184, 190 and 198 were acquired. During activity state $T_2$, MPS points 186, 192 and 196 were acquired. Thus, referring to FIG. 3B, centerline 200 is the projection of the catheter 3D trajectory on image $180_1$. Centerline 202 is the projection of the catheter 3D trajectory on image $180_2$. Centerline 204 is the projection of the catheter 3D trajectory on image $180_3$. Using these Centerlines, and image segmentation, the borders, such as borders 206 and 208 are detected. A circle is generated around each MPS point, using the distance between these borders, at a particular MPS point, as the diameter of the respective circle.

Referring back to FIG. 1, Catheter 106 is inserted into tubular organ 134 and MPS 124 acquires a plurality of MPS points within organ 134. Medical imaging system 118 acquires at least one 2D image of tubular organ 134 from at least one perspective. Simultaneously, organ timing signal detector 126 detects the activity state of the organ. Thus, each MPS point and each 2D image is associated with an organ timing signal reading. Organ timing signal detector 126 detects the organ timing signal from the acquired MPS points, by filtering periodic motions of the MPS sensor (not shown) relative to reference sensor 130. Detecting organ timing signals from MPS points is further described in U.S. patent application Ser. No. 10/986567, which is incorporated herein by reference. Alternatively, organ timing signal detector 126 is an Electrocardiogram (ECG) detector fitted with body surface electrodes. In accordance with another embodiment of the disclosed technique, each of medical imaging system 118 and MPS 124 has a different organ timing signal detector. Processor 128 registers the 3D MPS coordinate system with the 2D coordinate system. Processor 128 associates each MPS point with the corresponding 2D image according to the detected organ timing signals.

Figure 4:
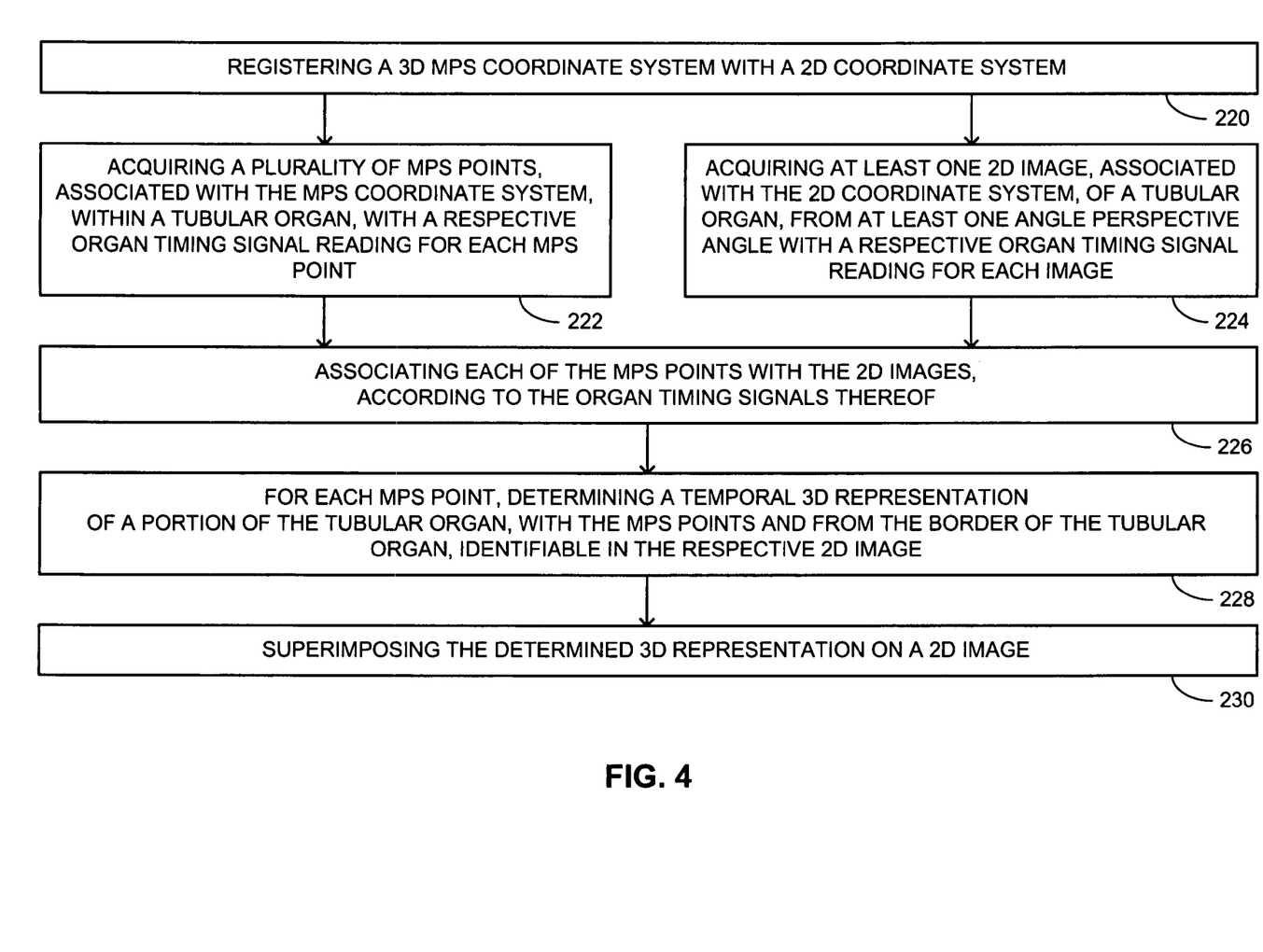
FIG. 4 is a schematic illustration of a method for determining a 3D representation of a tubular organ.

Reference is now made to FIG. 4, which is a schematic illustration of a method for determining a 3D representation of a tubular organ in accordance with a further embodiment of the disclosed technique. In procedure 220, a 3D MPS coordinate is registered with a 2D coordinate system. Consequently every point in the 3D MPS coordinate system is mapped to a point in the 2D coordinate system. With reference to FIG. 1, processor 128 registers the 3D MPS coordinate system with the 2D coordinate system.

In procedure 222, a plurality of MPS points, within a tubular organ, with a respective organ time signal reading for each MPS point, are acquired. The MPS points are acquired with a catheter, fitted with an MPS sensor, into the tubular organ. The MPS points are acquired during the insertion of the catheter or during a manual or automatic pullback of the catheter. The organ timing signal associated with each MPS point reading represents the activity state of the organ during the acquisition of the MPS point. With reference to FIG. 1, MPS 124 acquires a plurality of MPS points, within organ 134, with an MPS sensor coupled with distal end 108 of catheter 106. The organ timing signals are detected by organ timing signal detector 126.

In procedure 224, at least one 2D image of a tubular organ is acquired form at least one angle perspective angles of the organ, with a respective organ timing signal reading for each image. Prior to the acquisition of the at least one 2D image, a dye is injected into the tubular organ. This dye may be injected by the catheter acquiring the MPS points. With reference to FIG. 1, medical imaging system 118 acquires at least one 2D image of tubular organ 134 from at least one perspective. The organ timing signals are detected by organ timing signal detector 126. After procedures 220 and 222 the method proceeds to procedure 224.

In procedure 226, each of the MPS points is associated with the 2D images, according to the organ timing signals thereof. Thus, each MPS point is associated with a respective 2D image. With reference to FIG. 1, processor 128 associates each of the MPS points with a respective 2D image detected by imaging radiation detector 116.

In procedure 228, a temporal 3D representation of a portion of the tubular organ, is determined for each MPS point, with the MPS point and from the borders of the tubular organ, identifiable in the respective 2D image. Determining the 3D representation is further explained in conjunction with FIG. 5. With reference to FIG. 1, Processor 128 determines a 3D representation of a portion of the tubular organ, for each MPS point, from the MPS point and from the 2D border of the tubular organ, identifiable in the respective 2D image. 3D representation 132 is displayed on display 132.

In procedure 230, the determined 3D representation is superimposed on a 2D image. The 3D representation may be projected on any of the at least one 2D images. The 3D representation may further be projected on a real time 2D image. Therefore, the system selects a desired angle of perspective of the real time 2D and projects the 3D representation on that real time 2D image. Furthermore, when the 3D representation is projected on a real time 2D image, the 2D projection of the 3D representation can function as a virtual dye. Therefore, there is no need to inject a dye into the tubular organ prior to the acquisition of the real time 2D image. Furthermore, the disclosed technique further enables to identify bifurcation points of the tubular organ. Virtual dye and bifurcation points are further illustrated in conjunction with FIG. 6. It is noted that bifurcation points can be identified on the 3D representation. With reference to FIG. 1, processor 128 projects the determined 2D representation on one of the 2D images and displays it on display 122.

Figure 5:
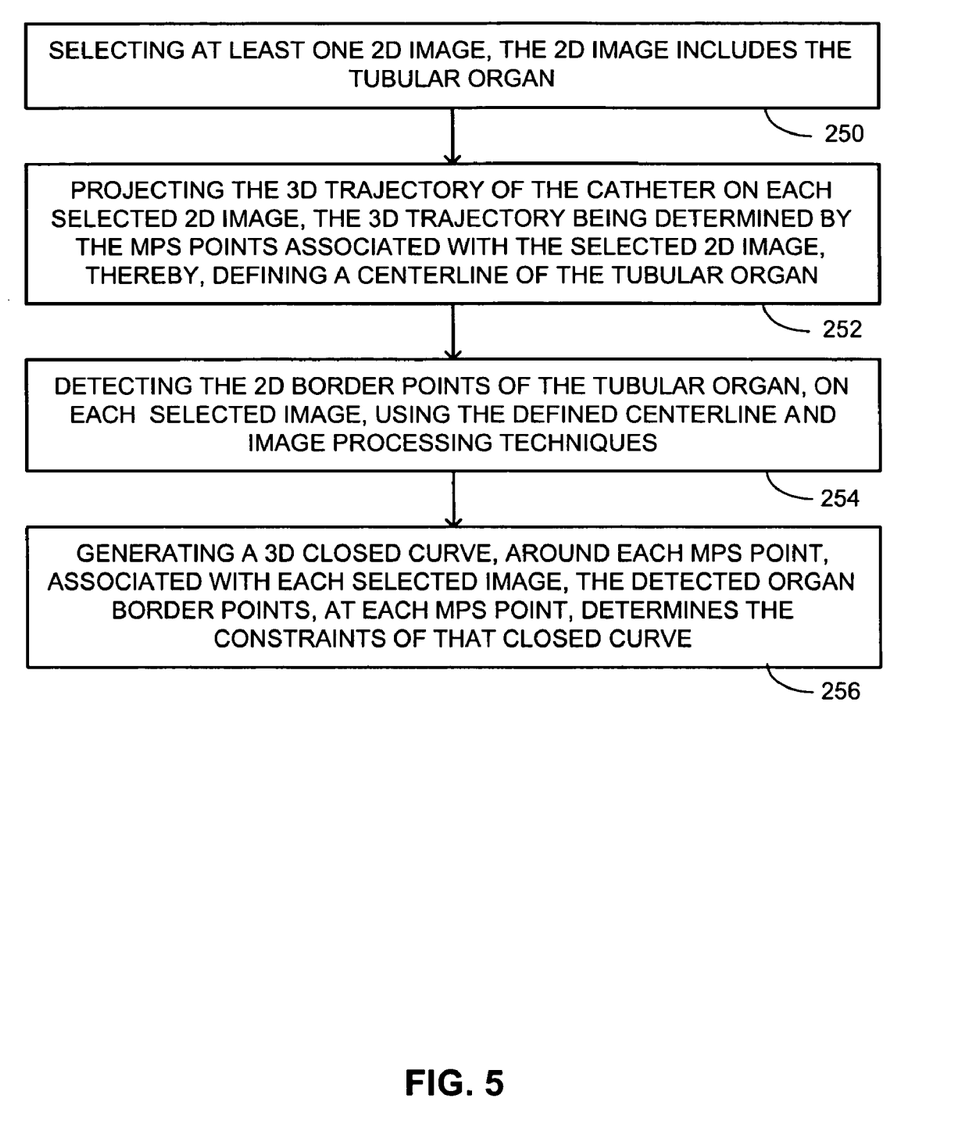
FIG. 5 is a method for determining a 3D model of a tubular organ.

Reference is now made to FIG. 5, which is a method for determining a 3D model of a tubular organ in accordance with another embodiment of the disclosed technique. In procedure 250, at least one 2D image is selected, the image includes the tubular organ. With reference to FIG. 1, processor 128 selects one or more 2D images.

In procedure 252, the 3D trajectory of the catheter, determined by the associated MPS points, is projected on each selected 2D image. Thereby, a centerline of the tubular organ is defined. With reference to FIG. 1, processor 128 projects the 3D trajectory of the catheter on the selected 2D image, thereby, defining the centerline of the tubular organ.

In procedure 254, the 2D border points of the tubular organ, on the selected image, are detected. These 2D border points are detected using the defined centerline and image processing techniques. These image processing techniques may be for example edge detection. With reference to FIG. 1, processor 128 detects the borders of the tubular organ on the selected image.

In procedure 256, a 3D closed curve is generated around each MPS point, associated with each selected image. The detected 2D border points, at each MPS point, determines the constraints of that closed curve (e.g., the circumference of the closed curve must included these border points). In the case wherein 2D images, of the tubular organ, were acquired from only one perspective, the closed curve is a circle. The diameter of that circle is the distance between the detected 2D borders of the tubular organ. When, for example, the 2D images of the tubular organ were acquired from two different perspectives, the refined contour will have the shape of an ellipse. In the case wherein more then two 2D images were acquired, the shape of the closed curve is arbitrary. With reference to FIG. 1, processor 128 generates a 3D closed curve around each MPS point associated with the selected image.

Figure 6:
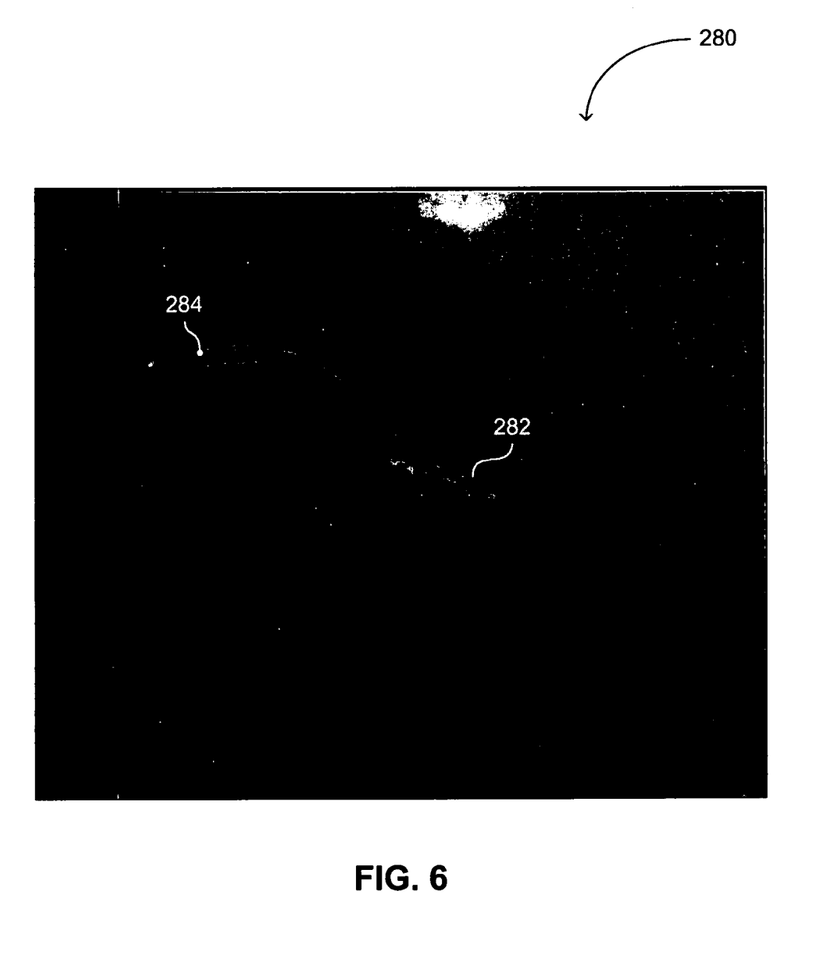
FIG. 6 is a schematic illustration of and image 380 of a tubular organ.

Reference is now made to FIG. 6, which is a schematic illustration of image 280 of a tubular organ in accordance with a further embodiment of the disclosed technique. 2D projection 282 of a 3D representation of the tubular organ is superimposed on image 280. 2D projection 282 serves as a virtual dye of the tubular organ. Thus, there is no need to inject a dye into the tubular organ prior to the acquisition of the image 280.

Furthermore, point 284 is identified as a bifurcation point. According to the disclosed technique, a bifurcation point is determined when after identifying only two borders for one MPS point, now for the next MPS point, the system identifies at least three borders, with a gap between two adjacent ones. The bifurcation point resides in the transition area between these two MPS points. The system then verifies that this is indeed a bifurcation point with the aid of another 2D image, from another perspective angle of the tubular organ.

In some cases, the inspected tubular organ may be infected with lesions or plaque. Consequently, the determined borders may be those of the lesion within the tubular organ and not the actual borders of the tubular organ.

Figure 7:
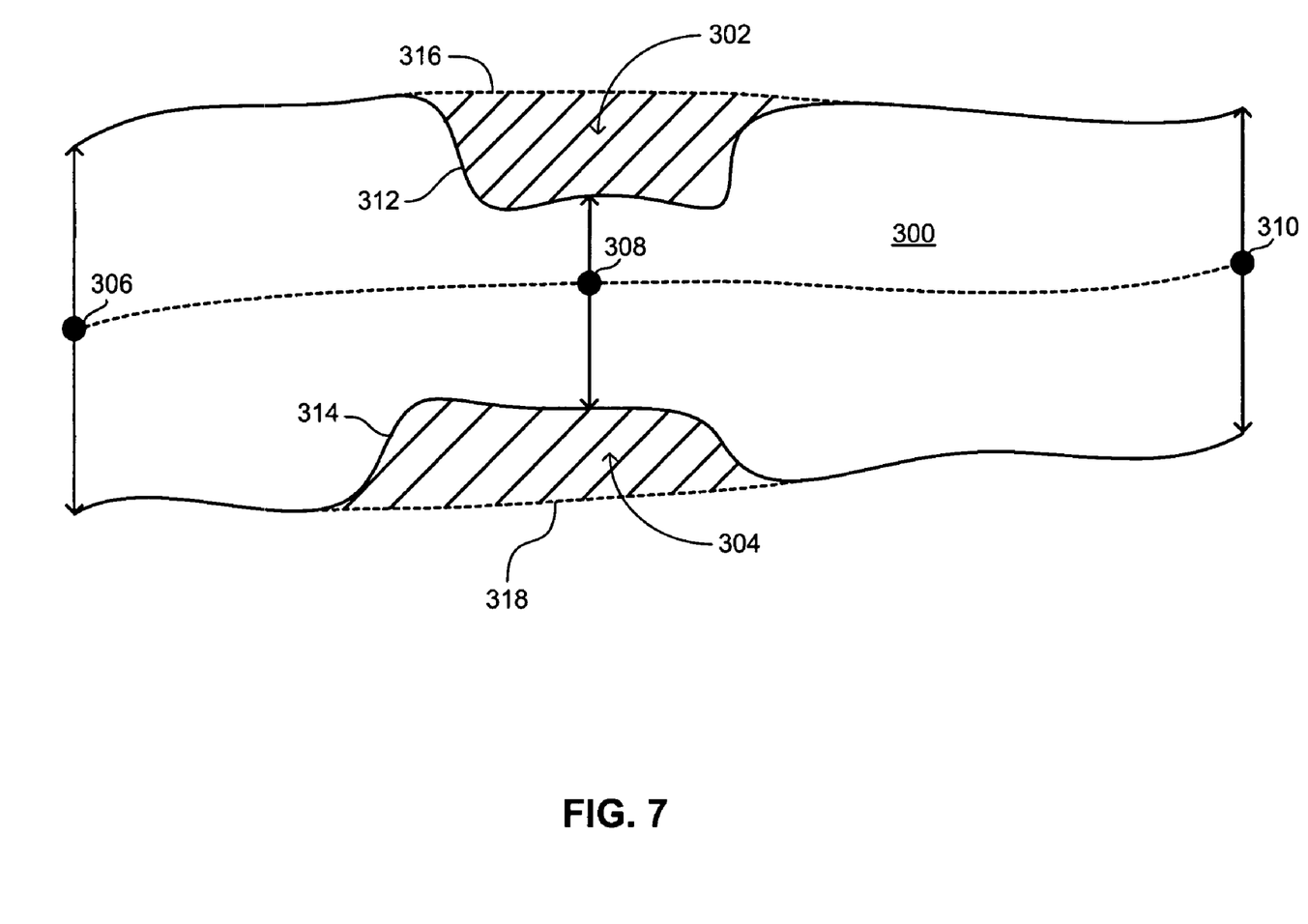
FIG. 7 is a schematic illustration of a tubular organ 300 infected by lesions 302 and 304.

Reference is now made to FIG. 7, which is a schematic illustration of a tubular organ 300 infected by lesions 302 and 304 in accordance with another embodiment of the disclosed technique. According to MPS points 306, 308 and 310, borders 312 and 314 were determined as the borders of tubular organ 300. However, borders 312 and 314 do not represent the true borders of tubular organ 300. When the 3D representation of the tubular organ is displayed, as described in conjunction with FIG. 4, the physician may notice that borders 312 and 314 are not the true borders of tubular organ 300. Therefore, the physician selects MPS points 306 and 310 as reference points for the true width of tubular organ 300. True borders 316 and 318 are determined (e.g., by interpolation) according to the width between borders 312 and 314 at MPS points 306 and 310. Furthermore, using true borders and the lesion borders, characteristics, such as the position, the length and the volume of the lesion can be determined. When, for example, a procedure of placing a stent device in an artery is performed, a mark, representing the location of the lesion may be superimposed on a real time image of the artery. Consequently, the physician can accurately navigate the stenting catheter to the location of the lesion.

When a 3D representation of an object is projected on a 2D image, the true dimensions of the object may be distorted. For example, a sphere will appear as a circle if projected onto a 2D image plane. When the object is a tubular organ within the human body, such as a coronary artery, that tubular organ may curve "into" or "out of" the image plane. Thus, the true length of the tubular organ may be distorted. This phenomenon is called foreshortening. Since the 3D representation of the tubular organ was constructed from a 3D trajectory of a catheter, within the tubular organ, the system provides the physician with information regarding the true length of the displayed tubular organ. Furthermore, the system provides the physician with a representation of the true length of the tubular organ on the 2D image.

Figure 8:
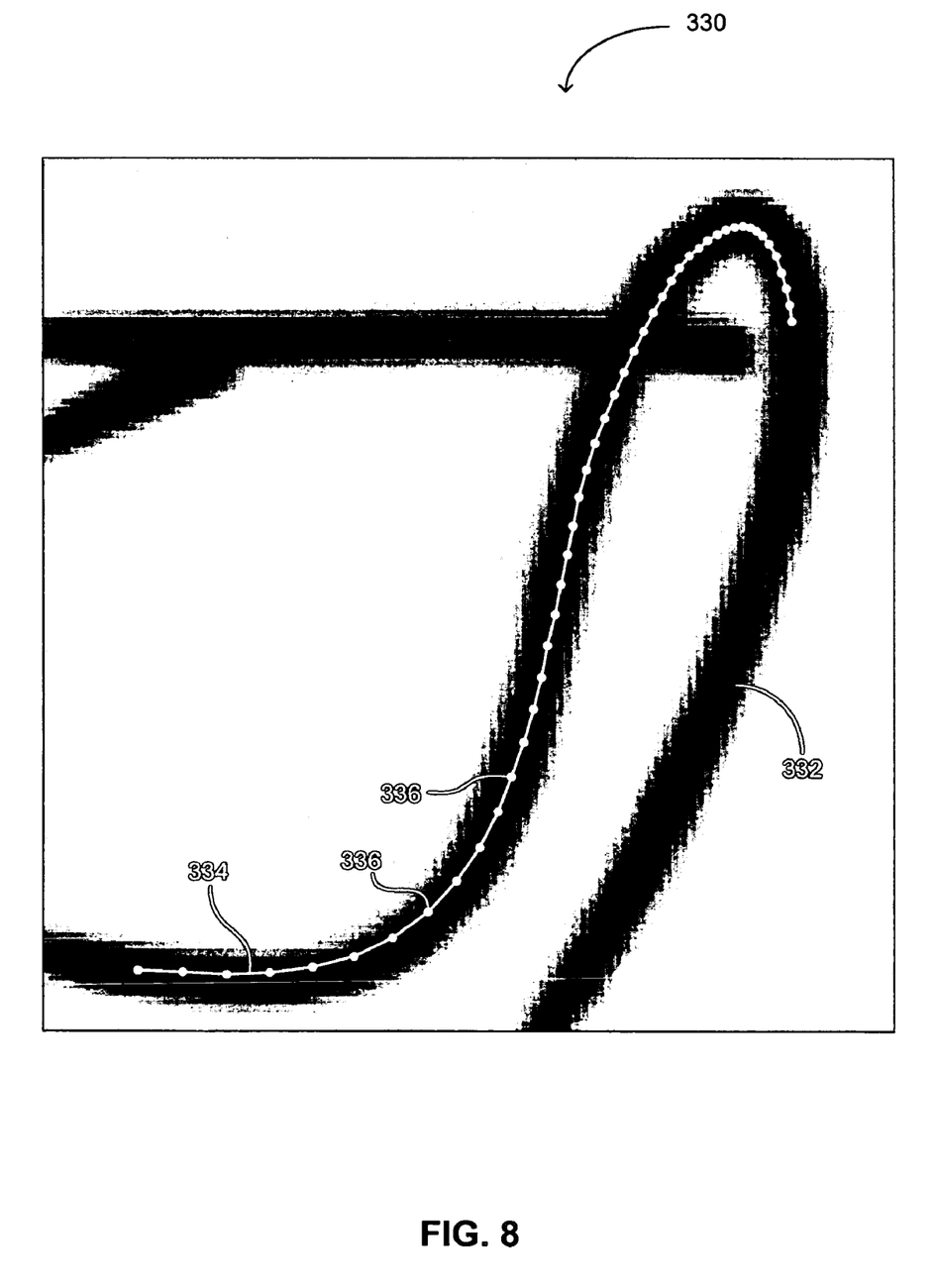
FIG. 8 is a schematic illustration of a 2D image generally reference 330 of tubular organ 332.

Reference is now made to FIG. 8, which is a schematic illustration of a 2D image generally reference 330 of tubular organ 332 in accordance with a further embodiment of the disclosed technique. In FIG. 7, 3D trajectory 334 of tubular organ 332 is projected on 2D image 330. A plurality of equally spaced markers points 336 are marked on 3D trajectory 334. The space between each pair of marker points 336 on 3D trajectory 334 is a tangible unit of length (e.g., 1 millimeter). 3D trajectory 334 and marker points 336 are projected on 2D image 330. Consequently, where the foreshortening phenomenon worsens, the distance between adjacent pairs of marker points 336, on the plane of 2D image 330, is observed to decrease. Thus, the physician has both a quantitative assessment of the true length of tubular organ 330 and a visual aid to asses the foreshortening phenomenon on 2D image 330. According to a further aspect of the disclosed technique, the system colors the marker points 336 differently for different levels of foreshortening. The level of foreshortening is determined, for example, according to the ratio between the lengths of the projection of the organ, on the 2D image, to the true length of the organ (i.e., the length of the 3D trajectory). Where this ratio is small, the foreshortening phenomenon is prominent and the markers are colored, for example, red. Where this ratio is large, the foreshortening phenomenon is not prominent and the markers are colored, for example, green.

The foreshortening phenomenon may worsen or lessen according the angle of perspective of the organ. According to another embodiment of the disclosed technique, with reference to FIG. 1, processor 128 automatically selects the perspective angle of medical imaging system 118 where the foreshortening phenomenon is the least prominent and recommends that perspective angle to the physician.

It will be appreciated by persons skilled in the art that the disclosed technique is not limited to what has been particularly shown and described hereinabove. Rather the scope of the disclosed technique is defined only by the claims, which follow.

The invention claimed is:

1. A method for determining a three dimensional representation of a tubular organ, said method comprising the procedures of:
registering a three dimensional medical positioning system (MPS) coordinate system with a two dimensional coordinate system;
acquiring a plurality of MPS points within said tubular organ, said MPS points are associated with said MPS coordinated system, each of said MPS points is acquired with a respective organ timing signal reading;
acquiring at least one two dimensional image of said tubular organ, said at least one two dimensional image is associated with said two dimensional coordinate system, said at least one two dimensional image is acquired from at least one perspective angle, each of said at least one two dimensional image is further acquired with a respective organ timing signal reading;
associating each of said MPS points with said at least one two dimensional image according to the organ timing signals thereof;
determining a temporal three dimensional representation of a portion of said tubular organ for each MPS point, said procedure of determining a three dimensional representation comprising the sub-procedures of:
selecting at least one two dimensional image, said at least one two dimensional image including said tubular organ;
projecting the trajectory of said catheter on the selected two dimensional image, said trajectory being determined by said MPS points associated with said selected two dimensional image, thereby defining a centerline of said tubular organ;
detecting the border points of tubular organ on said selected two dimensional image; and
generating a three dimensional closed curve around each of said MPS points, associated with said selected image.

2. The method according to claim 1 further includes injecting a dye into said tubular organ prior to said acquiring at least one two dimensional image.

3. The method according to claim 1 further includes the procedure of superimposing said three dimensional representation on a two dimensional image.

4. The method according to claim 3, wherein said two dimensional image is a real time two dimensional image, said real time two dimensional image being associated with an organ timing signal readings.

5. The method according to claim 3, wherein said two dimensional image is one of said at least one two dimensional image.

6. The method according to claim 3, wherein the perspective of said two dimensional image is selected such that a foreshortening phenomenon is minimized, said foreshortening phenomenon caused due to the super position of said three dimensional representation on the plane of said two dimensional image.

7. The method according to claim 3, wherein a two dimensional projection of said superimposed three dimensional representation serves as a virtual dye instead of injecting a dye prior to acquiring said real time two dimensional image.

8. The method according to claim 1, wherein said plurality of MPS points are acquired by inserting a catheter, fitted with an MPS sensor into said tubular organ.

9. The method according to claim 1, wherein said organ timing signal is an electrocardiogram signal.

10. The method according to claim 9, wherein said electrocardiogram signal is filtered from said plurality of MPS points.

11. The method according to claim 1, wherein said at least one two dimensional image is a type selected from the group consisting of:
X-ray image;
Magnetic resonance image;
Positron emission tomography image; and
Ultrasound image.

12. The method according to claim 1, wherein said procedure of determining a three dimensional representation of said portion of said tubular organ is determined from said MPS points and the borders of said tubular organ, said borders being identifiable on said at least one two dimensional image.

13. The method according to claim 1, wherein said border points are detected according to said defined centerline and image processing techniques.

14. The method according to claim 1, wherein a plurality of equally spaced marker points are determined on said three dimensional trajectory for providing a visual true length assessment of said tubular organ when said trajectory is projected on said two dimensional image, thereby providing a visual assessment of said foreshortening.

15. The method according to claim 14, wherein, said markers are colored according to the level of said foreshortening.

16. The method according to claim 14, wherein, the space between said markers is one millimeter.

17. A system for determining a three dimensional representation of a tubular organ, said system comprising:

an organ timing signal detector for acquiring organ timing signal reading, said organ timing signal reading represent the activity state of an organ;

a medical imaging system for acquiring at least one two dimensional image from at least one perspective, said medical imaging system being associated with a two dimensional coordinated system, said at least one two dimensional image being associated with a respective organ timing signal reading;

a medical positioning system (MPS), coupled with said organ timing signal detector, said MPS being associated with a three dimensional MPS coordinate system, for acquiring a plurality of MPS points, each of said MPS points being associated with a respective organ timing signal reading;

a catheter, fitted with an MPS sensor, for insertion into said tubular organ said MPS sensor is coupled said MPS;

a processor, coupled with said MPS, with said organ timing signal detector and with said medical imaging system, for registering said three dimensional MPS coordinate system with said two dimensional coordinate system, for associating an organ timing signal reading with each of said MPS points and with each of said at least one two dimensional image and for determining a three dimensional representation of said tubular organ by:

selecting at least one two dimensional image, said at least one two dimensional image includes said tubular organ;

projecting the trajectory of said catheter on the selected two dimensional image, said trajectory being determined by said MPS points associated with said selected two dimensional image, thereby defining a centerline of said tubular organ;

detecting the borders of tubular organ on said selected two dimensional image; and generating a three dimensional close curve around each of said MPS points, associated with said selected image.

18. The system according to claim 17, wherein, a dye is injected into said tubular organ prior to said acquisition of said at least one two dimensional image.

19. The system according to claim 17, further includes a display for displaying said three dimensional representation.

20. The system according to claim 19, wherein, said display is further operative to display said three dimensional image is superimposed on a two dimensional image.

21. The system according to claim 20, wherein, said two dimensional image is a real time two dimensional image.

22. The system according to claim 19, wherein, a two dimensional projection of said superimposed three dimensional representation serves as a virtual dye instead of injecting a dye prior to acquiring said real time two dimensional image.

23. The system according to claim 20, wherein, said processor is further operative to select the perspective of said two dimensional image, such that the foreshortening phenomenon is minimized, said foreshortening phenomenon is caused due to the projection of said three dimensional representation on the plane of said two dimensional image.

24. The system according to claim 17, wherein, said processor is further operative for superimposing said three dimensional representation on a real time two dimensional image, said real time two dimensional image being associated with an organ timing signal readings.

25. The system according to claim 17, wherein, said organ timing signal is an electrocardiogram signal.

26. The system according to claim 25, wherein, said processor is further operative to filters said electrocardiogram signal from said plurality of MPS points.

27. The system according to claim 17, wherein, said at least one two dimensional image is a type selected from the group consisting of:

X-ray image;
Magnetic resonance image;
Positron emission tomography image; and
Ultrasound image.

28. The system according to claim 17, wherein said processor is further operative for determining said three dimensional representation from said MPS points and the borders of said tubular organ, said borders being identifiable on said at least one two dimensional image.

29. The system according to claim 17, wherein said processor is further operative for detecting said border points according to said defined centerline and image processing techniques.

30. The system according to claim 17, wherein, said processor is further operative for determining a plurality of equally spaced marker points on said three dimensional trajectory for providing a visual true length assessment of said tubular organ when said trajectory is projected on said two dimensional image.

31. The system according to claim 30, wherein, said markers are colored according to the level of said foreshortening.

32. The method according to claim 30, wherein, the space between said markers is one millimeter.

* * * * *